United States Patent [19]

Steiner et al.

[11] Patent Number: 5,660,832
[45] Date of Patent: Aug. 26, 1997

[54] PROCESS FOR THE PREPARATION OF PESTICIDE-POOR CONCENTRATES OF ACTIVE COMPONENTS OF PLANTS

[75] Inventors: Rudolf Steiner, Bäch; Renato Colombi, Wädenswil, both of Switzerland

[73] Assignee: Emil Flachsmann AG, Switzerland

[21] Appl. No.: 502,850

[22] Filed: Jul. 14, 1995

[30] Foreign Application Priority Data

Jul. 14, 1994 [CH] Switzerland ............ 2-258/94

[51] Int. Cl.$^6$ ............................................. A61K 35/78
[52] U.S. Cl. ........................ 424/195.1; 424/DIG. 8
[58] Field of Search .................. 424/195.1, DIG. 8

[56] References Cited

U.S. PATENT DOCUMENTS 3,878,299  4/1975  Vilain et al. .............. 424/195.1
3,925,547  12/1975  Henkin et al. .............. 424/195.1

FOREIGN PATENT DOCUMENTS 261421  8/1987  European Pat. Off. .
382116  2/1990  European Pat. Off. .
1125117  3/1962  Germany .
3940092  6/1991  Germany .

*Primary Examiner*—John W. Rollins
*Attorney, Agent, or Firm*—Burns, Doane, Swecker & Mathis, L.L.P.

[57] ABSTRACT

Pesticide-poor concentrates of active components of plants are obtained in that in a first step plants or parts thereof, which may be charged in fresh or dried state, are extracted with at least one polar solvent at a measured pH-value in the range from 3.2 to 9.8 in such a way, that in the obtained primary extract are contained mainly the desired plant components, accompanied by undesired plant components, accompanying substances and pesticides, in a second step said primary extract is contacted with adsorber resin(s) in such a way, that on one hand the desired plant components are adsorbed thereon, and on the other hand the solution with the undesired plant components, the accompanying substances and pesticides are separated from the charged resin, in a third step the desired plant components are desorbed from said resin with at least one solvent, and in a fourth step the solvent(s) is (are) removed either partially or completely, and by this way a concentrate of active components is obtained. These concentrates of active components may be used in products of the pharma, cosmetic and food industry.

36 Claims, No Drawings

PROCESS FOR THE PREPARATION OF PESTICIDE-POOR CONCENTRATES OF ACTIVE COMPONENTS OF PLANTS

BACKGROUND OF THE INVENTION

1. Field of the Invention

The present invention is directed to a process for the preparation of pesticide-poor concentrates of active components of plants.

2. Description of the Prior Art

In the prior art no process is known with which certain, selected plant components would be obtainable selectively and in an as much as possible pure and pesticide-poor form as well as in high concentration.

In DE PS 17 67 098 is described a process, in which various extractions are carried out. Furthermore, in this process are used halogenated solvents, such as methylene chloride, chloroform and carbon tetrachloride.

In DE OS 39 40 092 is described a process, in which is obtained an extract from the leafs of ginkgo biloba. This extract has an increased content of flavone glycosides. This manystage process is very complicate.

SUMMARY OF THE INVENTION

It is an object of the present invention to provide a process, with which certain, selected plant components are obtainable selectively and in an as much as possible pure and pesticide-poor form as well as in high concentration.

The with the new process prepared concentrates of active components shall especially be allergen-poor and shall preferably contain no alkyl phenols.

Furthermore, this new process shall be simple in its technical realization.

In the realization of this process the total power comsumption shall be low.

Furthermore, this process shall show not much steps. Additionally only relatively low amounts of organic solvents shall be used.

Quite surprisingly there was found now a process, with which all the above objects are reached and with which the above mentioned drawbacks are overcome.

The inventive process for the preparation of pesticide-poor concentrates of active components of plants is characterized in that in a first step plants or parts thereof, which may be charged in fresh or dried state, are extracted with at least one polar solvent at a measured pH-value in the range from 3.2 to 9.8 in such a way, that in the obtained primary extract are contained mainly the desired plant components, accompanied by undesired plant components, accompanying substances and pesticides,
  in a second step said primary extract is contacted with adsorber resin(s) in such a way, that on one hand the desired plant components are adsorbed thereon, and on the other hand the solution with the undesired plant components, the accompanying substances and pesticides is separated from the charged resin,
  in a third step the desired plant components are desorbed from said resin with at least one solvent, and
  in a fourth step the solvent(s) is (are) removed either partially or completely, and by this way a concentrate of active components is obtained.

DETAILED DESCRIPTION OF THE PREFERRED EMBODIMENTS

Preferred embodiments of this process are defined in the dependent claims.

The primary extract may be prepared according to processes known in the prior art, for example by means of percolation, maceration or a dynamic extraction; see Marcel Loncin "Die Grundlagen der Verfahrenstechnik in der Lebensmittelindustrie" (1969), especially pages 204 to 256, Verlag Sauerländer Aarau and Frankfurt am Main, and references cited herein, as well as Erich Ziegler "Die natürlichen und künstlichen Aromen" (1982), especially pages 221 to 242, Dr. Alfred Hüthig Verlag Heidelberg, and references cited herein.

If desired the inventive process may be interrupted at the end of the first step for a desired period of time. The primary extract may be prepared at any place, concentrated, occasionally transported, and at the place of its further processing in the desired moment it may be backdiluted to the at times desired concentration and then it may be further processed according to the inventive process.

Polar solvents which may be used in preparing the primary extract include water, alcohols, ketones and mixtures thereof. Preferred alcohols include a $C_1$ to $C_4$ alcohol, most preferably ethanol or methanol. Preferred ketones include a $C_3$ to $C_5$ ketone, most preferably acetone.

The primary extract for contact with the adsorber resin may contain an alcohol or ketone at a concentration of 0 to 30% by weight of primary extract, preferably 10 to 20% by weight.

Adjustment of the pH in the first step of the process of the invention may be performed by the addition of at least one acid or base, such as an organic carboxylic acid or an inorganic base. Preferred organic carboxylic acids include formic acid, acetic acid, tartaric acid, citric acid, and ascorbic acid. Preferred inorganic bases include diluted aqueous solutions of sodium hydroxide, potassium hydroxide and carbonates, such as sodium carbonate, potassium carbonate and ammonium carbonate, and hydrogen carbonates such as sodium hydrogen carbonate, potassium hydrogen carbonate and ammonium hydrogen carbonate.

The primary extract is contacted with the adsorber resin at a temperature from 5° C. to 50° C., preferably from 15° C. to 30° C.

The adsorber resins, which are commercially available, may be re-used several times.

The adsorber resins include non-polar and polar resins, such as polyamides and polyvinylpyrrolidones. Preferred are polystyrene- and acrylester-resins.

Preferred adsorber resins have a surface from 100 to 1000 $m^2$ per gram and a grain size from 0.2 mm to 1.5 mm.

By the process of the invention, between the second and third step the charged resin may be washed with at least one solvent. Preferred solvents include water and aqueous mixtures which contain up to 60% by weight, preferably from 10 to 20% by weight, of one or more alcohols, one or more ketones, or mixtures thereof. Preferred alcohols include a $C_1$ to $C_4$ alcohol, most preferably ethanol or methanol. Preferred ketones include a $C_3$ to $C_5$ ketone, most preferably acetone. The washing between the second and third steps may be carried out at a temperature from 5° C. to 50° C., preferably from 15° C. to 30° C.

According to the invention, the solvent used for desorption of desired components in the third step of the process includes water, an acid, a base, an acidic buffer, or a basic buffer. Acidic buffers are preferably used at a pH of 1 to 3, and basic buffers are preferably used at a pH of 9 to 12. Alcohols or ketones may also be used as the solvent for desorption of desired components in the third step. Preferred alcohols include a $C_1$ to $C_6$ alcohol, more preferably ethanol or methanol. Preferred ketones include a $C_3$ to $C_5$ ketone, more preferably acetone. The solvent for desorption of desired components may include mixtures of the aforementioned components with a water content ranging from 0 to 100% by weight, preferably from 10 to 20% by weight. Water vapor may also be used as the desorption agent.

Desorption of the desired components is carried out at a temperature from 5° C. to 160° C., preferably from 15° C. to 100° C., most preferably from 15° C. to 30° C.

In the fourth step of the process of the invention, the solvent may be partially or completely removed by means of distillation, preferably under reduced pressure.

At the end of the fourth step of the process of the invention, the concentrate of active components may be transformed into a powder, for example by means of spray drying.

According to the invention, organic solvents, if present, may be removed at least partially between the first and second steps, preferably by means of distillation under reduced pressure.

The inventive process has additionally the enormous advantage, that therewith undesired accompanying substances, such as starch, sugar, and especially residues of pesticides, such as insecticides, herbicides, fungicides, and so on may be separated.

The inventive prepared concentrates of active components may be used in products of the pharma, cosmetic and food industry.

Plants which are subjected to the process of the invention include those which contain one or more of alkaloids, flavanoids, saponins, bitterings and terpenes. Preferred plants include *Boldo folia, Spartii radix herba, Chinae cortex, Chelidonii herba, Chrysanthemum parthenium, Rauwolfiae radix, Betulae folia, Crataegi folia, Solidaginis herba, Passiflorae herba, Tiliae flores, Violae tricol. herba, Ginkgo folia, Ginseng radix, Senegae radix, Hippocastani semen, Hederae belie. herba, Liquiritiae radix, Gentianae radix*, and *Salicis cortex*.

In one aspect of the invention, a pesticide-poor and allergen-poor concentrate of active components of ginkgo folia is prepared by a process according to the invention which includes preparing a primary extract of fresh or dried ginkgo leaves at a pH ranging from 7.1 to 9.8.

In another aspect of the invention, a pesticide-poor and allergen-poor concentrate of active components of ginkgo folia is preferred by a process according to the invention which includes preparing a primary extract of ginkgo folia which contains from 0 to 22% by weight of one or more alcohol, one or more ketone, or mixtures thereof.

The following examples illustrate the present invention.

EXAMPLE 1

Description for the Preparation of a High Content Ginkgo Bilobae Extract a) Extraction 35.0 kg ginkgo bilobae leafs were filled into the extractor and were extracted in the percolation process with the 10-fold amount of a mixture of 12% m/m ethanol-water and 1% ammonium carbonate at a temperature of 70° C. up to exhaustion. The measured pH-value of the extraction agent was about 8.4.

There was obtained as an intermediate product 350 kg of a primary extract.

b) Adsorbtion and Desorbtion

The primary extract was pumped over a column, which was charged with 100 kg adsorber resin amberlite XAD 16 of Röhm and Haas. The temperature of the primary extract lied between 15° C. and 25° C. The rate of flow was between 400–800 liter per hour.

The plant components were now adsorbed from the resin, and the flowing off residual solution was thrown away.

After an intermediate washing with about 125 liter of distilled water at room temperature there was desorbed with 25 liter of ethanol.

Then was rewashed with 100 liter of distilled water at room temperature.

The ethanol phase and the wash water contained now the desorbed plant components.

The solution was now evaporated under vacuum up to a solids content of about 60%.

The adsorber resin may be re-used several times.

c) Drying

The above obtained solution with a solids content of about 60% was dried to a powder in conventional manner in a spray drying tower with an air inlet temperature from 180° C. to 200° C.

There were obtained 1000 g of a brown powder.

The content of flavon glycosides was determined by means of HPLC according to "Hagers Handbuch der Pharmazeutischen Praxis" of R. Hänsel et. al., Drogen E-O volume 5, Springer Verlag, page 276.

EXAMPLE 2

Description for the Preparation of a High Content Crataegi Extract a) Extraction 25.0 kg crataegi folia cum flores were filled into the extractor and were extracted in the percolation process with the 10-fold amount of a mixture of 60% m/m ethanol-water at a temperature of 60° C. up to exhaustion.

There was obtained as an intermediate product 250 kg of a primary extract.

The ethanol was distilled off under vacuum nearly completely. The residue was diluted with water to a solids content of about 10%.

b) Adsorbtion

The obtained mixture was pumped over a column, which was charged with 60 kg adsorber resin amberlite XAD 7 of Röhm and Haas. The temperature of the solution lied between 15° C. and 25° C. The rate of flow was between 120–400 liter per hour.

The plant components were now adsorbed from the resin, and the flowing off residual solution was thrown away.

After an intermediate washing with about 65 liter of distilled water at room temperature there was desorbed with 18 liter of ethanol.

Then was rewashed with 65 liter of distilled water.

The ethanol phase and the wash water contained now the desorbed plant components.

The solution was now evaporated under vacuum up to a solids content of about 60%.

The adsorber resin may be re-used several times.

c) Drying

The above obtained solution with a solids content of about 60% was dried to a powder in conventional manner in a spray drying tower with an air inlet temperature from 180° C. to 200° C.

There were obtained 1000 g of a brown powder.

The content of flavonoids was determined according to Deutschem Arzneibuch Nr. 10 (DAB 10), calculated as hyperosid, as being 7.6%.

EXAMPLE 3

Description for the Preparation of a High Content Hippocastani E. Semen Extract a) Extraction 7.50 kg of grinded semen hippocastani were filled into the extractor and were extracted in the percolation process with the 10-fold amount of a mixture of 70% m/m ethanol-water at a temperature of 60° C. up to exhaustion.

There was obtained as an intermediate product 75 kg of a primary extract.

The ethanol was distilled off under vacuum nearly completely. The residue was diluted with water to a solids content of about 6%.

b) Adsorbtion

The obtained mixture was pumped over a column, which was charged with 60 kg adsorber resin amberlite XAD 7 of Röhm and Haas. The temperature of the solution lied between 15° C. and 25° C. The rate of flow was between 120–360 liter per hour.

The plant components were now adsorbed from the resin, and the flowing off residual solution was thrown away.

After an intermediate washing with about 65 liter of distilled water at room temperature there was desorbed with 18 liter of ethanol.

Then was rewashed with 65 liter of distilled water.

The ethanol phase and the wash water contained now the desorbed plant components.

The solution was now evaporated under vacuum up to a solids content of about 60%.

The adsorber resin may be re-used several times.

c) Drying

The above obtained solution with a solids content of about 60% was dried to a powder in conventional manner in a spray drying tower with an air inlet temperature from 180° C. to 200° C.

There were obtained 1000 g of a brown powder.

The content of triterpene saponins was determined according to DAB 10, calculated as aescin, as being more than 70%.

EXAMPLE 4

Description for the Preparation of a High Content Salicis Extract a) Extraction 55.0 kg cortex salicis were filled into the extractor and were extracted in the percolation process with the 10-fold amount of a mixture of 58% m/m ethanol-water at a temperature of 60° C. up to exhaustion.

There was obtained as an intermediate product 550 kg of a primary extract.

The ethanol was distilled off under vacuum nearly completely. The residue was diluted with water to a solids content of about 10%.

b) Adsorbtion

The obtained mixture was pumped over a column, which was charged with 60 kg adsorber resin Dowex-XUS of Dow Chemicals. The temperature of the solution lied between 15° C. and 20° C. The rate of flow was between 80–240 liter per hour.

The plant components were now adsorbed from the resin, and the flowing off residual solution was thrown away.

After an intermediate washing with about 65 liter of distilled water at room temperature there was desorbed with 20 liter of ethanol.

Then was rewashed with 65 liter of distilled water.

The ethanol phase and the wash water contained now the desorbed plant components.

The solution was now evaporated under vacuum up to a solids content of about 60%.

The adsorber resin may be re-used several times.

c) Drying

The above obtained solution with a solids content of about 60% was dried to a powder in conventional manner in a spray drying tower with an air inlet temperature from 180° C. to 200° C.

There were obtained 1000 g of a brown powder.

The content of salicin [analysed according to B. Meier and O. Sticher, Pharm. Acta Helv..60, 269 (1985)] can be determined as being more than 30%.

EXAMPLE 5

Description for the Preparation of a High Content Ginseng Extract a) Extraction 40.0 kg ginseng radix were filled into the extractor and were extracted in the percolation process with the 10-fold amount of a mixture of 30% m/m ethanol-water at a temperature of 70° C. up to exhaustion.

There was obtained as an intermediate product 400 kg of a primary extract.

The ethanol was distilled off under vacuum up to a residual content of 15% m/m. The residue was diluted with water to a solids content of about 10%.

b) Adsorbtion

The obtained mixture was pumped over a column, which was charged with 60 kg adsorber resin amberlite XAD 7 of Röhm and Haas. The temperature of the solution lied between 15° C. and 25° C. The rate of flow was between 100–240 liter per hour.

The plant components were now adsorbed from the resin, and the flowing off residual solution was thrown away.

After an intermediate washing with about 55 liter of distilled water at room temperature there was desorbed with 20 liter of ethanol.

Then was rewashed with 55 liter of distilled water.

The ethanol phase and the wash water contained now the desorbed plant components.

The solution was now evaporated under vacuum up to a solids content of about 60%.

The adsorber resin may be re-used several times.

c) Drying

The above obtained solution with a solids content of about 60% was dried to a powder in conventional manner in a spray drying tower with an air inlet temperature from 180° C. to 200° C.

There were obtained 1000 g of a yellow-brown powder.

The content of ginsenosides, analysed according to DAB 10, was determined as being more than 70%.

There were determined the following contents of fungicides in the starting material and in the obtained product.

|  | Quintozen (Microgram/kg) | Pentachloraniline (Microgram/kg) |
| --- | --- | --- |
| Radix ginseng (starting material) | 4900 | 1600 |
| Extract of radix ginseng (obtained product) | 26 | 440 |

The above figures show that with the inventive process the undesired residues of pesticides may be strongly reduced.

We claim:

1. A process for the preparation of a pesticide-poor concentrate of active components of a plant, comprising:
   a first step, wherein a fresh or dried plant or part thereof is extracted with at least one polar solvent at a pH ranging from 3.2 to 9.8 to produce a primary extract which contains predominantly desired plant components, and by-products of undesired plant components and pesticides,
   a second step, wherein said primary extract is contacted with an adsorber resin so that the desired plant components are adsorbed on the resin, and the remaining solution containing the undesired plant components and pesticides is separated from the charged resin;
   a third step, wherein the desired plant components are desorbed from said resin with at least one desorption solvent; and
   a fourth step, wherein said desorption solvent is partially or completely removed to produce a concentrate of active components.

2. The process according to claim 1, wherein the polar solvent is selected from the group consisting of water, an alcohol, a ketone, and mixtures thereof.

3. The process according to claim 2, wherein the alcohol is a $C_1$ to $C_4$ alcohol and the ketone is a $C_3$ to $C_5$ ketone.

4. The process according to claim 3, wherein the alcohol is ethanol or methanol and the ketone is acetone.

5. The process according to claim 1, wherein the first step of the pH is adjusted to from 3.2 to 9.8 by the addition of at least one acid or base.

6. The process according to claim 5, wherein the acid is an organic carboxylic acid and the base is an inorganic base.

7. The process according to claim 6, wherein the organic carboxylic acid is selected from the group consisting of formic acid, acetic acid, tartaric acid, citric acid and ascorbic acid, and the inorganic base is selected from the group consisting of sodium hydroxide, potassium hydroxide, carbonates and hydrogen carbonates.

8. The process according to claim 7, wherein the carbonates are selected from the group consisting of sodium carbonate, potassium carbonate and ammonium carbonate, and the hydrogen carbonates are selected from the group consisting of sodium hydrogen carbonate, potassium hydrogen carbonate and ammonium hydrogen carbonate.

9. The process according to claim 1, wherein the primary extract to be contacted with the adsorber resin contains up to 30% by weight of one or more alcohol, one or more ketone, or a mixture thereof.

10. The process according to claim 9, wherein the primary extract to be contact with the adsorber resin contains from 10 to 20% by weight of one or more alcohol, one or more ketone, or a mixture thereof.

11. The process according to claim 1, wherein the second step the primary extract is contacted with the adsorber resin at a temperature from 5° C. to 50° C.

12. The process according to claim 11, wherein the temperature is from 15° C. to 30° C.

13. The process according to claim 1, wherein the adsorber resin is a non-polar or polar resin with a surface area from 100 to 1000 $m^2$ per gram of adsorber resin, and a grain size from 0.2 mm to 1.5 mm.

14. The process according to claim 13, wherein the non-polar or polar resin is selected from the group consisting of polyamides, polyvinylpyrrolidones, polystyrenes and acrylesters.

15. The process according to claim 1, wherein the charged resin is washed with at least one washing solvent after the second step and before the third step.

16. The process according to claim 15, wherein the at least one washing solvent is water or an aqueous mixture which contains 60% or less by weight of an alcohol, a ketone, or a mixture thereof.

17. The process according to claim 16, wherein the aqueous mixture contains from 10 to 20% by weight of a $C_1$ to $C_4$ alcohol, a $C_3$ to $C_5$ ketone, or a mixture thereof.

18. The process according to claim 17, wherein the $C_1$ to $C_4$ alcohol is ethanol or methanol, and $C_3$ to $C_5$ ketone is acetone.

19. The process according to claim 15, wherein the charged resin is washed with at least one washing solvent at a temperature from 5° C. to 50° C.

20. The process according to claim 19, wherein the temperature is from 15° C. to 30° C.

21. The process according to claim 1, wherein the desorption solvent is selected from the group consisting of water, an acid, a base, an acidic buffer, a basic buffer, an alcohol, a ketone, and mixtures thereof.

22. The process according to claim 21, wherein the desorption solvent has a water content up to 100% by weight, the alcohol is a $C_1$ to $C_6$ alcohol, and the ketone is a $C_3$ to $C_5$ ketone.

23. The process according to claim 22, wherein the desorption solvent has a water content from 10 to 20% by weight, the alcohol is ethanol or methanol, and the ketone is acetone.

24. The process according to claim 1, wherein the desorption solvent is water vapor.

25. The process according to claim 1, wherein the third step desorption of the desired components is carried out at a temperature from 5° C. to 160° C.

26. The process according to claim 25, wherein the third step desorption of the desired components is carried out at a temperature from 15° C. to 100° C.

27. The process according to claim 26, wherein the third step desorption of the desired components is carried out at a temperature from 15° C. to 30° C.

28. The process according to claim 1, wherein the fourth step the desorption solvent is partially or completely removed by means of distillation under reduced pressure.

29. The process according to claim 1, wherein the plant contains a component selected from the group consisting of alkaloids, flavanoids, saponins, bitterings, terpenes, and mixtures thereof.

30. The process according to claim 29, wherein the plant is selected from the group consisting of *Boldo folia, Spartii radix herba, Chinae cortex, Chelidonii herba, Chrysanthemum parthenium, Rauwolfiae radix, Betulae folia, Crataegi folia, Solidaginis herba, Passiflorae herba, Tiliae flores, Violae tricol. herba, Ginkgo folia, Ginseng radix, Senegae radix, Hippocastani semen, Hederae helic. herba, Liquiritiae radix, Gentianae radix,* and *Salicis corex.*

31. The process according to claim 1, wherein the concentrate of active components is transformed into a powder.

32. The process according to claim 31, wherein the concentrate of active components is transformed into a powder by means of spray drying.

33. The process according to claim 1, wherein organic solvents present in the primary extract are at least partially removed after the first step and before the second step.

34. The process according to claim 33, wherein the organic solvents are removed by means of distillation under reduced pressure.

35. The process according to claim 1, wherein the plant is ginkgo folia and in the first step a primary extract of ginkgo folia fresh or dried leaves is prepared at a pH ranging from 7.1 to 9.8, for the preparation of a concentrate of active components of ginkgo folia which is pesticide-poor and allergen-poor.

36. The process according to claim 1, wherein the plant is ginkgo folia and in the first step a primary extract of ginkgo folia is prepared using an aqueous solvent containing up to 20% of one or more alcohol, one or more ketone, or mixtures thereof, for the preparation of a concentrate of active components of ginkgo folia which is pesticide-poor and allergen-poor.

* * * * *